(12) United States Patent
Burkhead, Jr. et al.

(10) Patent No.: US 10,064,734 B2
(45) Date of Patent: Sep. 4, 2018

(54) GLENOID IMPLANT FOR A SHOULDER PROSTHESIS, AND SURGICAL KIT

(71) Applicant: Tornier SAS, Montbonnot Saint Martin (FR)

(72) Inventors: Wayne Z. Burkhead, Jr., Dallas, TX (US); Pascal Boileau, Nice (FR); Gilles Walch, Lyons (FR); Pierric Deransart, Grenoble (FR)

(73) Assignee: Tornier SAS, Montbonnot Saint Martin (FR)

( * ) Notice: Subject to any disclaimer, the term of this patent is extended or adjusted under 35 U.S.C. 154(b) by 0 days.

(21) Appl. No.: 15/336,531

(22) Filed: Oct. 27, 2016

(65) Prior Publication Data

US 2017/0042690 A1   Feb. 16, 2017

Related U.S. Application Data

(63) Continuation of application No. 13/363,159, filed on Jan. 31, 2012, now Pat. No. 9,498,345.

(Continued)

(30) Foreign Application Priority Data

Feb. 8, 2011   (FR) .............................. 20110050994

(51) Int. Cl.
*A61F 2/40* (2006.01)
*A61F 2/30* (2006.01)

(52) U.S. Cl.
CPC .. *A61F 2/4081* (2013.01); *A61F 2002/30332* (2013.01); *A61F 2002/30352* (2013.01);
(Continued)

(58) Field of Classification Search
CPC .. A61F 2/4081; A61F 2/40; A61F 2002/4088; A61F 2/4085; A61F 2002/30352
See application file for complete search history.

(56) References Cited

U.S. PATENT DOCUMENTS 4,986,833 A   1/1991   Worland
5,033,036 A   7/1991   Ohmori et al.
(Continued)

FOREIGN PATENT DOCUMENTS

EP   0581667   2/1994
EP   1488764 B1   12/2006
(Continued)

OTHER PUBLICATIONS

International Search Report and Written Opinion issue in PCT Application No. PCT/US2016/036500, dated Mar. 22, 2017, in 18 pages.

(Continued)

*Primary Examiner* — Alvin Stewart
(74) *Attorney, Agent, or Firm* — Knobbe Martens Olson & Bear LLP

(57) ABSTRACT

A glenoid implant for a shoulder prosthesis for implantation in the glenoid of a scapula according to embodiments of the present invention includes a central fixation element; an articular body configured for articulation with a humerus, the articular body comprising a plate, the plate comprising a side configured to be oriented toward the glenoid, the side comprising a central protrusion, wherein the central fixation element comprises a means for mechanically engaging with the central protrusion; a first means for locking rotation of the central fixation element with respect to the glenoid; and a second means for locking rotation of the articular body with respect to the glenoid.

12 Claims, 5 Drawing Sheets

Related U.S. Application Data

(60) Provisional application No. 61/438,570, filed on Feb. 1, 2011.

(52) U.S. Cl.
CPC ........... *A61F 2002/30354* (2013.01); *A61F 2002/30377* (2013.01); *A61F 2002/30485* (2013.01); *A61F 2002/30504* (2013.01); *A61F 2002/30616* (2013.01); *A61F 2002/30878* (2013.01); *A61F 2002/30886* (2013.01); *A61F 2220/0025* (2013.01); *A61F 2220/0033* (2013.01); *A61F 2310/00023* (2013.01); *A61F 2310/00179* (2013.01)

(56) References Cited

U.S. PATENT DOCUMENTS

| | | | |
|---|---|---|---|
| 5,080,673 A | 1/1992 | Burkhead et al. | |
| 5,458,637 A | 10/1995 | Hayes | |
| 5,489,309 A | 2/1996 | Lackey et al. | |
| 5,489,311 A | 2/1996 | Cipolletti | |
| 5,531,973 A | 7/1996 | Sarv | |
| 5,800,551 A | 9/1998 | Williamson et al. | |
| 5,954,722 A * | 9/1999 | Bono | A61B 17/7059 |
| | | | 606/281 |
| 6,102,954 A | 8/2000 | Albrektsson et al. | |
| 6,171,342 B1 | 1/2001 | O'Neil et al. | |
| 6,228,119 B1 | 5/2001 | Ondrla et al. | |
| 6,406,495 B1 | 6/2002 | Schoch | |
| 6,508,841 B2 | 1/2003 | Martin et al. | |
| 6,514,287 B2 | 2/2003 | Ondrla et al. | |
| 6,673,115 B2 | 1/2004 | Resch et al. | |
| 6,679,916 B1 | 1/2004 | Frankle et al. | |
| 6,699,289 B2 | 3/2004 | Iannotti et al. | |
| 6,761,740 B2 | 7/2004 | Tornier | |
| 6,790,234 B1 | 9/2004 | Frankle | |
| 6,860,903 B2 | 3/2005 | Mears et al. | |
| 6,953,478 B2 | 10/2005 | Bouttens et al. | |
| 7,169,184 B2 | 1/2007 | Pria | |
| 7,175,663 B1 | 2/2007 | Stone | |
| 7,175,665 B2 | 2/2007 | German et al. | |
| 7,204,854 B2 | 4/2007 | Guederian et al. | |
| 7,316,715 B2 | 1/2008 | Plaskon | |
| 7,462,197 B2 | 12/2008 | Tornier | |
| 7,462,199 B2 | 12/2008 | Justin et al. | |
| 7,604,665 B2 | 10/2009 | Iannotti et al. | |
| 7,608,109 B2 | 10/2009 | Dalla Pria | |
| 7,621,961 B2 | 11/2009 | Stone | |
| 7,637,928 B2 | 12/2009 | Fernandez | |
| 7,648,530 B2 | 1/2010 | Habermeyer et al. | |
| 7,666,522 B2 | 2/2010 | Justin et al. | |
| 7,753,959 B2 | 7/2010 | Berelsman et al. | |
| 7,766,969 B2 | 8/2010 | Justin et al. | |
| 7,854,768 B2 | 12/2010 | Wiley et al. | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 7,993,408 B2 | 8/2011 | Meridew et al. | |
| 8,007,523 B2 * | 8/2011 | Wagner | A61B 17/7059 |
| | | | 606/290 |
| 8,048,161 B2 * | 11/2011 | Guederian | A61F 2/4081 |
| | | | 623/17.11 |
| 8,062,376 B2 | 11/2011 | Shultz et al. | |
| 8,070,820 B2 * | 12/2011 | Winslow | A61F 2/40 |
| | | | 623/19.11 |
| 8,092,545 B2 | 1/2012 | Coon et al. | |
| 8,206,453 B2 | 6/2012 | Cooney, III et al. | |
| 8,231,683 B2 | 7/2012 | Lappin et al. | |
| 8,241,365 B2 | 8/2012 | Williams, Jr. et al. | |
| 8,287,600 B2 * | 10/2012 | Angibaud | A61F 2/389 |
| | | | 623/20.15 |
| 8,308,807 B2 | 11/2012 | Seebeck et al. | |
| 8,357,201 B2 | 1/2013 | Mayer et al. | |
| 8,361,157 B2 * | 1/2013 | Bouttens | A61F 2/4081 |
| | | | 623/19.11 |
| 8,425,614 B2 | 4/2013 | Winslow et al. | |
| 8,444,680 B2 | 5/2013 | Dooney, Jr. et al. | |
| 8,449,617 B1 | 5/2013 | McDaniel et al. | |
| 8,454,702 B2 | 6/2013 | Smits et al. | |
| 8,465,548 B2 * | 6/2013 | Long | A61F 2/4081 |
| | | | 623/19.11 |
| 8,480,750 B2 | 7/2013 | Long | |
| 8,532,806 B1 | 9/2013 | Masson | |
| 8,556,902 B2 | 10/2013 | Ek et al. | |
| 8,556,980 B2 | 10/2013 | Deffenbaugh | |
| 8,556,981 B2 | 10/2013 | Jones et al. | |
| 8,591,591 B2 | 11/2013 | Winslow et al. | |
| 8,597,334 B2 | 12/2013 | Mocanu | |
| 8,632,597 B2 | 1/2014 | Lappin | |
| 8,690,951 B2 | 4/2014 | Baum et al. | |
| 8,753,402 B2 | 6/2014 | Winslow et al. | |
| 8,790,402 B2 | 7/2014 | Monaghan et al. | |
| 8,840,676 B2 | 9/2014 | Belew | |
| 8,961,611 B2 | 2/2015 | Long | |
| 9,114,017 B2 | 8/2015 | Lappin | |
| 9,498,345 B2 * | 11/2016 | Burkhead, Jr. | A61F 2/4081 |
| 9,629,725 B2 | 4/2017 | Gargac et al. | |
| 2002/0095214 A1 | 7/2002 | Hyde, Jr. | |
| 2003/0149485 A1 * | 8/2003 | Tornier | A61F 2/30721 |
| | | | 623/18.11 |
| 2004/0106928 A1 | 6/2004 | Ek | |
| 2004/0220673 A1 * | 11/2004 | Pria | A61F 2/40 |
| | | | 623/19.12 |
| 2004/0220674 A1 | 11/2004 | Pria | |
| 2005/0049709 A1 | 3/2005 | Tornier | |
| 2005/0143831 A1 | 6/2005 | Justin et al. | |
| 2005/0149044 A1 | 7/2005 | Justin et al. | |
| 2005/0261775 A1 | 11/2005 | Baum et al. | |
| 2005/0278030 A1 | 12/2005 | Tornier | |
| 2006/0074353 A1 | 4/2006 | Deffenbaugh et al. | |
| 2006/0100714 A1 | 5/2006 | Ensign | |
| 2006/0122705 A1 | 6/2006 | Morgan | |
| 2006/0142865 A1 | 6/2006 | Hyde, Jr. | |
| 2006/0200248 A1 | 9/2006 | Beguin et al. | |
| 2006/0200249 A1 | 9/2006 | Beguin et al. | |
| 2007/0016304 A1 | 1/2007 | Chudik | |
| 2007/0055380 A1 * | 3/2007 | Berelsman | A61F 2/4081 |
| | | | 623/19.11 |
| 2007/0100458 A1 | 5/2007 | Dalla Pria | |
| 2007/0142921 A1 | 6/2007 | Lewis et al. | |
| 2007/0156246 A1 | 7/2007 | Meswania et al. | |
| 2007/0179624 A1 | 8/2007 | Stone et al. | |
| 2007/0219638 A1 | 9/2007 | Jones et al. | |
| 2007/0244563 A1 | 10/2007 | Roche et al. | |
| 2008/0269906 A1 | 10/2008 | Iannotti et al. | |
| 2008/0294268 A1 | 11/2008 | Baum et al. | |
| 2008/0306601 A1 | 12/2008 | Dreyfuss | |
| 2009/0149961 A1 | 6/2009 | Dallmann | |
| 2009/0204225 A1 | 8/2009 | Meridew et al. | |
| 2009/0216332 A1 | 8/2009 | Splieth et al. | |
| 2009/0281630 A1 | 11/2009 | Delince et al. | |
| 2010/0016975 A1 | 1/2010 | Iannotti et al. | |
| 2010/0023068 A1 | 1/2010 | Bouttens et al. | |
| 2010/0049327 A1 | 2/2010 | Isch et al. | |
| 2010/0087927 A1 | 4/2010 | Roche et al. | |
| 2010/0161066 A1 | 6/2010 | Iannotti et al. | |
| 2010/0217399 A1 | 8/2010 | Groh | |
| 2010/0234959 A1 | 9/2010 | Roche et al. | |
| 2010/0274359 A1 * | 10/2010 | Brunnarius | A61F 2/30734 |
| | | | 623/19.13 |
| 2010/0291401 A1 | 11/2010 | Medina et al. | |
| 2010/0331990 A1 | 12/2010 | Mroczkowski | |
| 2011/0035013 A1 | 2/2011 | Winslow et al. | |
| 2011/0118846 A1 | 5/2011 | Katrana et al. | |
| 2011/0144760 A1 | 6/2011 | Wong et al. | |
| 2011/0190899 A1 | 8/2011 | Pierce et al. | |
| 2011/0282393 A1 | 11/2011 | Garlach et al. | |
| 2012/0004733 A1 | 1/2012 | Hodorek et al. | |
| 2012/0029647 A1 | 2/2012 | Winslow et al. | |
| 2012/0165954 A1 | 6/2012 | Nimal | |
| 2012/0191201 A1 | 7/2012 | Smits et al. | |
| 2012/0209392 A1 | 8/2012 | Angibaud et al. | |

(56) References Cited

U.S. PATENT DOCUMENTS

| | | | |
|---|---|---|---|
| 2012/0221111 A1* | 8/2012 | Burkhead, Jr. | A61F 2/4081 623/19.11 |
| 2012/0221112 A1 | 8/2012 | Lappin | |
| 2012/0232670 A1 | 9/2012 | Bojarski et al. | |
| 2012/0239156 A1 | 9/2012 | De Wilde et al. | |
| 2012/0253467 A1 | 10/2012 | Frankle | |
| 2012/0277880 A1* | 11/2012 | Winslow | A61F 2/4081 623/19.11 |
| 2013/0018483 A1 | 1/2013 | Li et al. | |
| 2013/0053968 A1 | 2/2013 | Nardini et al. | |
| 2013/0096631 A1 | 4/2013 | Leung et al. | |
| 2013/0110470 A1 | 5/2013 | Vanasse et al. | |
| 2013/0150972 A1 | 6/2013 | Iannotti et al. | |
| 2013/0150973 A1 | 6/2013 | Splieth et al. | |
| 2013/0150975 A1 | 6/2013 | Iannotti et al. | |
| 2013/0226309 A1 | 8/2013 | Daigo et al. | |
| 2013/0231754 A1 | 9/2013 | Daigo et al. | |
| 2013/0253656 A1 | 9/2013 | Long | |
| 2013/0261751 A1 | 10/2013 | Lappin | |
| 2013/0261752 A1 | 10/2013 | Lappin et al. | |
| 2013/0264749 A1 | 10/2013 | Jones et al. | |
| 2013/0282135 A1 | 10/2013 | Sun et al. | |
| 2014/0025173 A1* | 1/2014 | Cardon | A61F 2/4081 623/19.13 |
| 2014/0142711 A1 | 5/2014 | Maroney et al. | |
| 2014/0194995 A1 | 7/2014 | Koka | |
| 2014/0257499 A1 | 9/2014 | Winslow et al. | |
| 2014/0277180 A1 | 9/2014 | Paolino et al. | |
| 2014/0371863 A1 | 12/2014 | Vanasse et al. | |
| 2015/0094819 A1 | 4/2015 | Iannotti et al. | |
| 2015/0142122 A1 | 5/2015 | Bickley et al. | |
| 2015/0150688 A1 | 6/2015 | Vanasse et al. | |
| 2015/0272741 A1* | 10/2015 | Taylor | A61F 2/4081 623/19.11 |
| 2015/0305877 A1* | 10/2015 | Gargac | A61F 2/4081 623/19.11 |
| 2016/0270922 A1* | 9/2016 | Pressacco | A61F 2/30749 |
| 2016/0287401 A1* | 10/2016 | Muir | A61F 2/40 |
| 2016/0324649 A1* | 11/2016 | Hodorek | A61F 2/4081 |
| 2017/0042690 A1* | 2/2017 | Burkhead, Jr. | A61F 2/4081 |
| 2017/0172764 A1* | 6/2017 | Muir | A61F 2/4684 |

FOREIGN PATENT DOCUMENTS

| | | |
|---|---|---|
| EP | 1762201 A1 | 3/2007 |
| EP | 1515758 B1 | 3/2009 |
| EP | 1639966 B1 | 9/2009 |
| EP | 1927328 B1 | 1/2011 |
| EP | 1902689 B1 | 11/2011 |
| EP | 1996125 B1 | 5/2013 |
| EP | 2335655 B1 | 7/2013 |
| EP | 1951161 B1 | 4/2014 |
| EP | 1973498 B1 | 4/2014 |
| EP | 2481376 B1 | 4/2014 |
| FR | 2739151 A1 | 3/1997 |
| FR | 2776506 B1 | 8/2000 |
| FR | 2971144 A1 | 8/2012 |
| FR | 2977791 | 7/2014 |
| WO | WO 2011/073169 | 6/2011 |
| WO | WO 2011/150180 | 12/2011 |
| WO | WO 2015/068035 | 5/2015 |
| WO | WO 2015/103090 | 7/2015 |
| WO | WO 2017/007565 | 1/2017 |

OTHER PUBLICATIONS

Anatomical Shoulder™ Inverse/Reverse System Surgical Technique, Product Brochure, Zimmer, Inc., published 2006, in 32 pages.

Boileau, et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.

Boileau, et al., "Metal-backed glenoid implant with polyethylene insert is not a viable long-term therapeutic option," Journal of Shoulder and Elbow Surgery, Feb. 2015, pp. 1-10.

Castagna et al., "Mid-term results of a metal-backed glenoid component in total shoulder replacement," The Journal of Bone and Joint Surgery, Oct. 2010, vol. 92-B, No. 10, pp. 1410-1415.

Clement et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.

Eclipse™ Stemless Shoulder Prosthesis, Surgical Technique Guide, Anthrex GmbH, 2014, in 12 pages.

Epoca Shoulder Arthroplasty System, Synthes, Inc., Apr. 2008, in 4 pages.

Epoca Shoulder Arthroplasty System—Stem and Glenoid Technique Guide, Synthes, Inc., Apr. 2008, in 56 pages.

Extended European Search Report for EP Appl. No. 16161842.6 dated Sep. 30, 2016 in 7 pages.

Kany et al., "A convertible shoulder system: is it useful in total shoulder arthroplasty revisions?" International Orthopaedics, published online Oct. 16, 2014, vol. 39, pp. 299-304.

Katz et al., "New design of a cementless glenoid component in unconstrained shoulder arthroplasty: a prospective medium-term analysis of 143 cases," published online Oct. 27, 2012, vol. 23, pp. 27-34.

Montoya et al., "Midterm results of a total shoulder prosthesis fixed with a cementless glenoid component," Journal of Shoulder and Elbow Surgery, May 2013, vol. 22, Issue 5, pp. 628-635.

SMR Axioma ® TT Metal Back Surgical Technique, Product Brochure, Lima Corporate, dated Sep. 2013, in 48 pages.

Taunton et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.

Teissier et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.

The Anatomical Shoulder™: A true system approach, Product Brochure, Zimmer UK Ltd, printed 2006, in 6 pages.

Univers Revers™ Total Shoulder System, Surgical Technique Guide, Anthrex Inc., Version D, revised Jul. 2, 2015, in 28 pages.

EP Search Report and Written Opinion issued in European Patent Application No. 12153346.7, dated Mar. 8, 2012, in 6 pages.

French Search Report and Written Opinion issued in Application. No. FR1150994, dated May 27, 2011, in 7 pages.

* cited by examiner

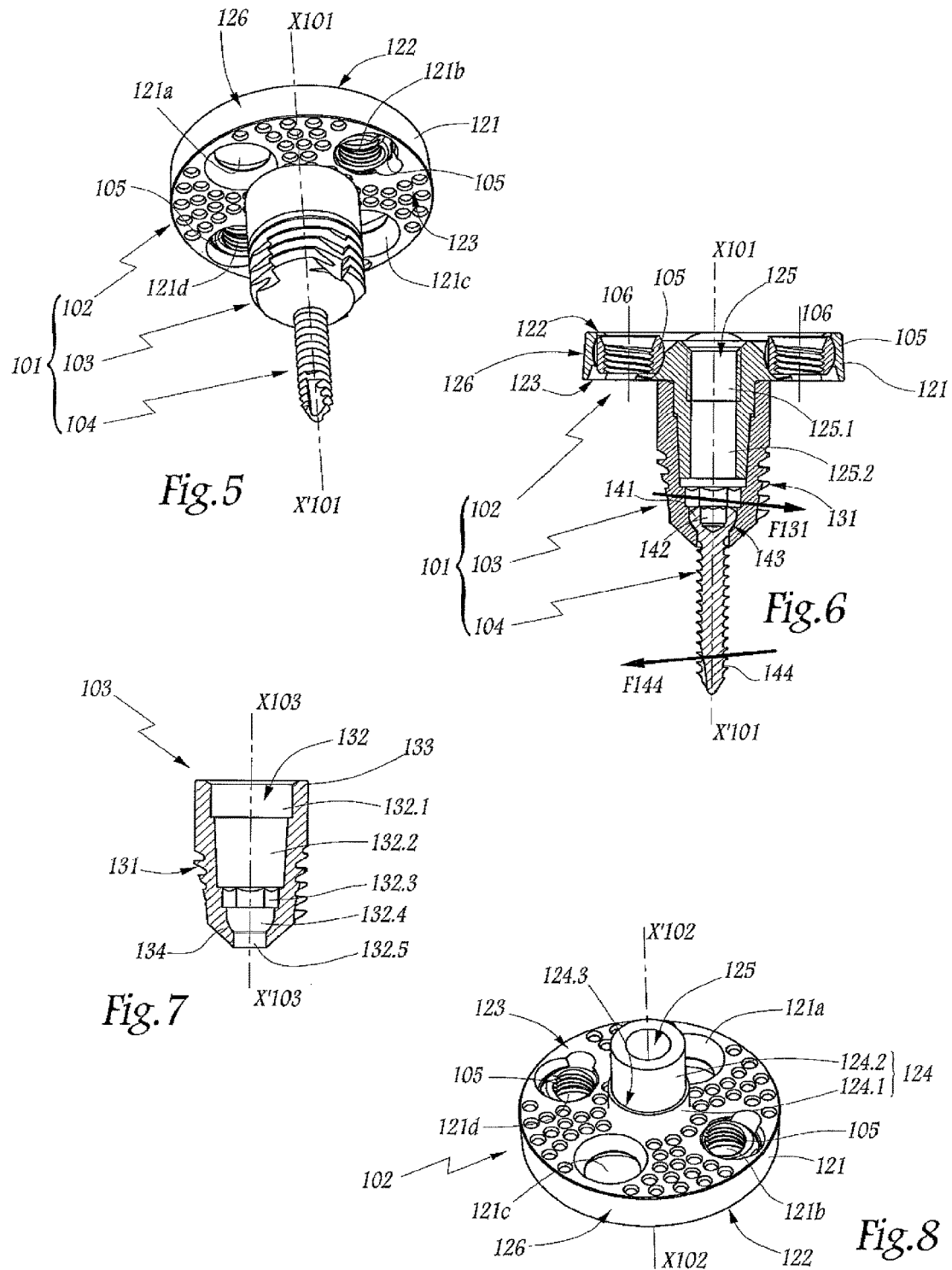

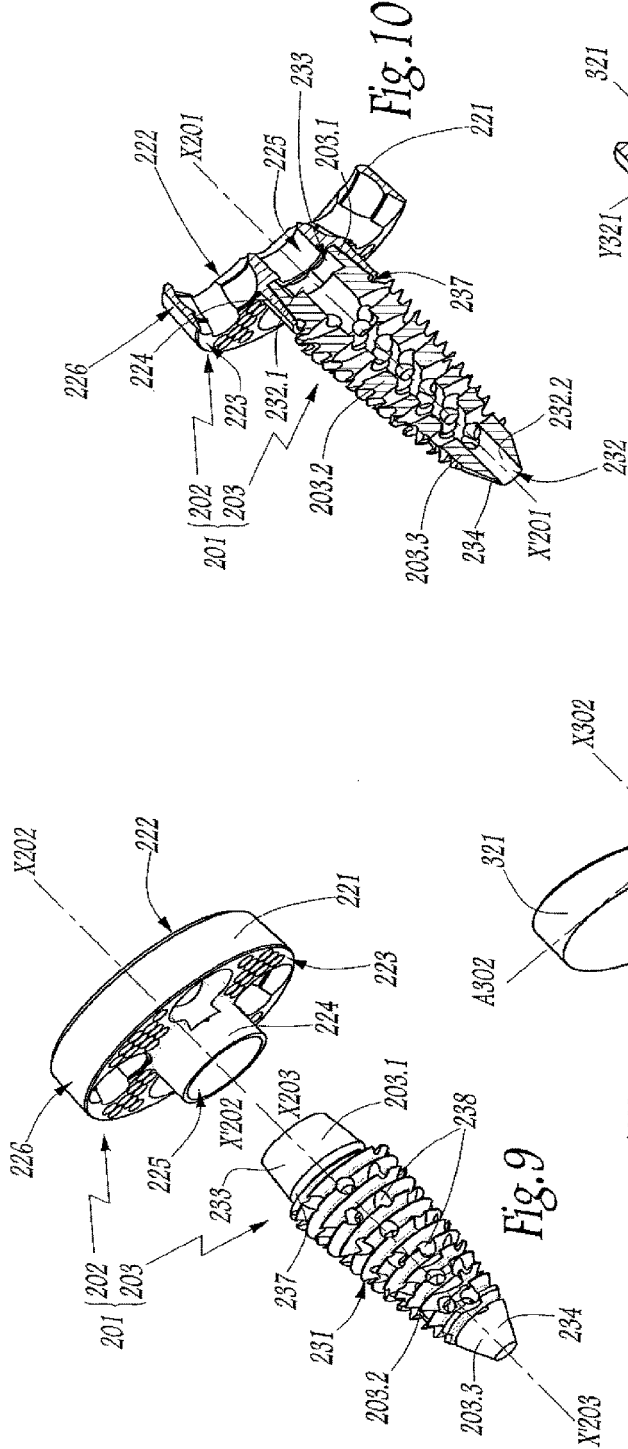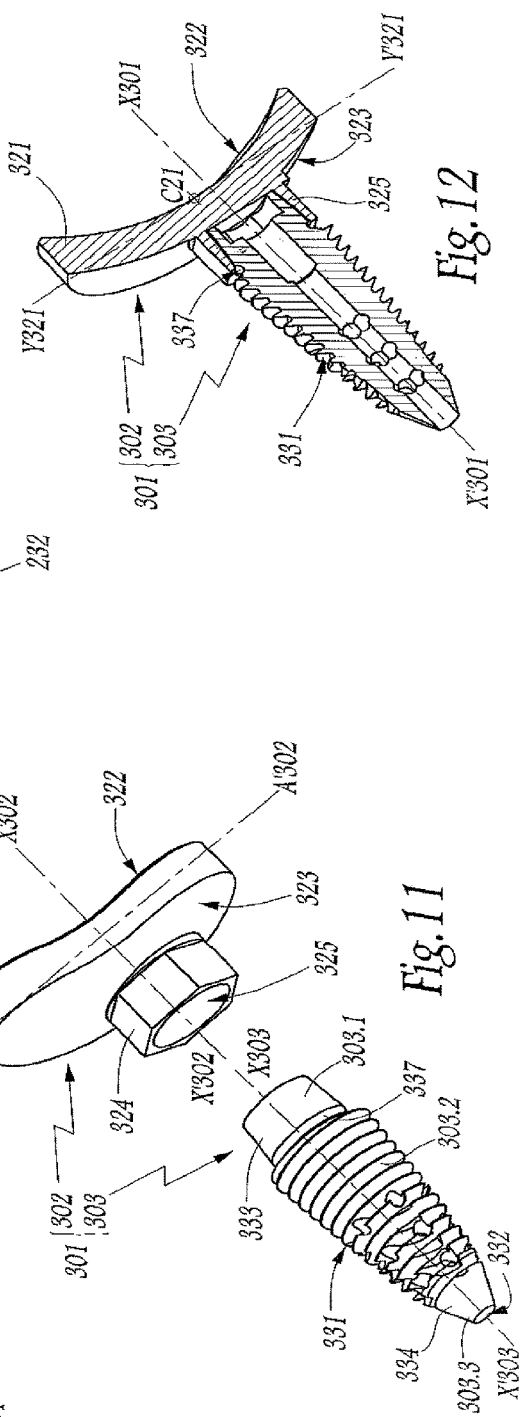

GLENOID IMPLANT FOR A SHOULDER PROSTHESIS, AND SURGICAL KIT

CROSS-REFERENCE TO RELATED APPLICATIONS

This application is a continuation of U.S. application Ser. No. 13/363,159, filed Jan. 31, 2012, which claims the benefit of U.S. Provisional Patent Application Ser. No. 61/438,570, filed on Feb. 1, 2011, and claims foreign priority to French Patent Application No. 20110050994, filed on Feb. 8, 2011, both of which are incorporated herein by reference in their entireties for all purposes.

TECHNICAL FIELD

Embodiments of the present invention relate generally to a glenoid implant for a shoulder prosthesis, as well as a surgical kit comprising such a glenoid implant.

BACKGROUND

Typically, a shoulder prosthesis includes a glenoid implant intended to replace the glenoid cavity of the scapula and/or a humeral implant intended to replace the humeral head. The glenoid implant generally includes an articular body intended to articulate with the humeral head, and a fixation means to stabilize the articular body with respect to the scapula.

SUMMARY

A glenoid implant for a shoulder prosthesis for implantation in the glenoid of a scapula according to embodiments of the present invention includes a central fixation element, an articular body configured for articulation with a humerus, the articular body including a plate, the plate including a side configured to be oriented toward the glenoid, the side including a central protrusion, wherein the central fixation element includes a means for mechanically engaging with the central protrusion, a first means for locking rotation of the central fixation element with respect to the glenoid, and a second means for locking rotation of the articular body with respect to the glenoid.

A glenoid implant according to embodiments of the present invention includes a central fixation element, an articular body configured for articulation with a humerus, the articular body including a central protrusion, wherein the central fixation element and the central protrusion are configured for mechanical interengagement, a first locking mechanism configured to lock rotation of the central fixation element with respect to the glenoid, and a second locking mechanism configured to lock rotation of the articular body with respect to the glenoid.

A method for implanting a glenoid implant according to embodiments of the present invention includes implanting a central fixation element into the glenoid, mechanically engaging a central protrusion of an articular body with the central fixation element, locking rotation of the central protrusion with respect to the central fixation element, and locking rotation of the articular body with respect to the glenoid.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 illustrates a perspective view of a glenoid implant according to another embodiment of the present invention.

FIG. 6 illustrates an axial cross-sectional view of the glenoid implant of FIG. 5, according to embodiments of the present invention.

FIG. 7 illustrates an axial cross-sectional view of a central fixation element of the glenoid implant of FIG. 5, according to embodiments of the present invention.

FIG. 8 illustrates a perspective view of an articular body of the glenoid implant of FIG. 5, according to embodiments of the present invention.

FIG. 9 illustrates an exploded perspective view of a glenoid implant according to another embodiment of the present invention.

FIG. 10 illustrates a perspective axial cross-sectional view of the glenoid implant of FIG. 9, according to embodiments of the present invention.

FIG. 11 illustrates an exploded perspective view of a glenoid implant according to another embodiment of the present invention.

FIG. 12 illustrates a perspective axial cross-sectional view of the glenoid implant of FIG. 11, according to embodiments of the present invention.

Figure 1:
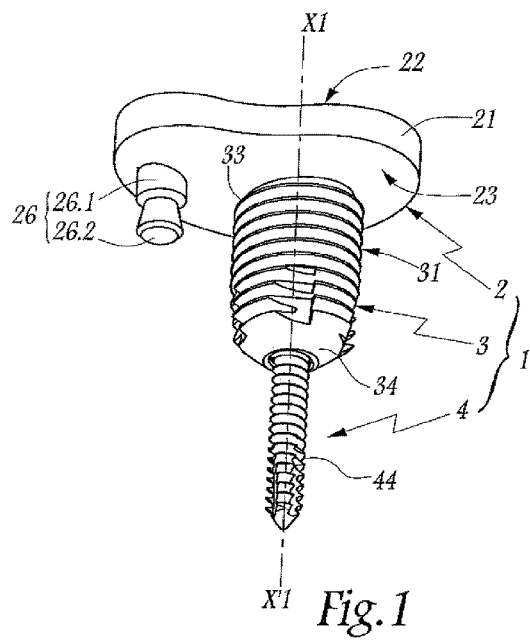
FIG. 1 illustrates a perspective view of a glenoid implant according to embodiments of the present invention.
Figure 2:
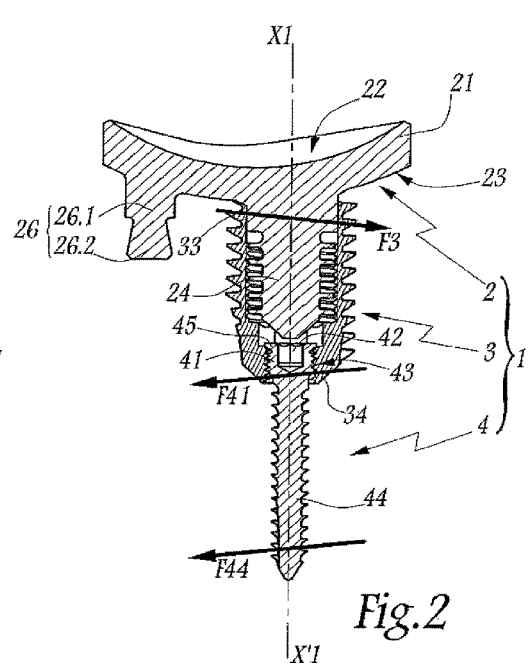
FIG. 2 illustrates a front axial cross-sectional view of the glenoid implant of FIG. 1, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1-4 show a glenoid implant 1, referred to as anatomical (or not reversed), configured to be implanted in the glenoid of a scapula (or shoulder blade, not shown), of a human being. The glenoid implant 1 includes an articular body 2, a central fixation element 3 for anchoring the articular body 2 in the scapular glenoid, and a locking screw 4 configured to deter rotation of the central element 3 with respect to the scapula, according to embodiments of the present invention. The articular body 2, after having been implanted in the glenoid, is configured to articulate with a head, eventually a prosthetic head, of a humerus (not shown) of the patient, in order to reproduce articular performance as close as possible to the original performance of the patient's shoulder.

As used herein, the terms "superior" and "inferior" are used to refer to the orientation of the glenoid implant as shown in FIG. 1, in which the articular body 2 is toward a top of a longitudinal geometric axis X1-X'1, and the screw 4 is toward a bottom of the axis X1-X'1, according to embodiments of the present invention. In other words, an element is located superior to another element if it is closer to X1 than the other element, and an element is inferior to another element if it is closer to X'1 than the other element. As used herein, the term "tronconical" is used to refer to a shape or surface that is or is like a truncated cone shape or surface.

Figure 4:
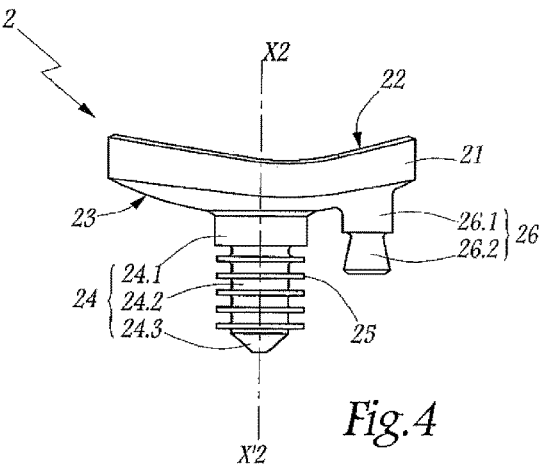
FIG. 4 illustrates a front elevation view of an articular body of the glenoid implant of FIG. 1, according to embodiments of the present invention.

The articular body 2, which is shown by itself in FIG. 4, includes a plate 21 that is substantially perpendicular to the longitudinal geometric axis X2-X'2 of the articular body. The plate 21 defines a superior surface 22 that is concave, which constitutes an articular surface for the articulation of the scapula with the humeral head, and by an inferior surface 23, provided with a central protrusion 24, which extends along the axis X2-X'2. The central protrusion 24 includes a superior portion 24.1 which is cylindrical with a circular cross-section, an intermediate portion 24.2 which is cylindrical with a circular cross-section that is smaller in diameter than that of the superior portion 24.1, and an inferior portion 24.3 that is tronconical and of which the diameter becomes smaller as it extends further from the plate 21, according to embodiments of the present invention. The intermediate portion 24.2 is provided with five fins 25 perpendicular to the axis X2-X'2 and parallel to each other, which are separated along the length of the central portion 24.2 and each of which extends about the perimeter of the intermediate portion 24.2, according to embodiments of the present invention.

The articular body 2 is formed of one or two synthetic materials, such as, for example, polyethylene, polyether ether ketone ("PEEK"), or polyurethane, which gives the fins 25 an elasticity to permit them to deform slightly.

The inferior surface 23 is also provided with a lateral post 26 which extends along a direction that is parallel to the axis X2-X', according to embodiments of the present invention. The lateral post 26 includes a superior portion 26.1 which is connected to the inferior surface 23 of the plate 21, and an inferior portion 26.2 connected to the superior portion 26.1. The superior portion 26.1 is cylindrical with a circular cross-section, and its diameter is smaller than the diameter of the central protrusion 24. The inferior portion 26.2 is tronconical, and its diameter increases as it extends further from the plate 21, according to embodiments of the present invention.

Figure 3:
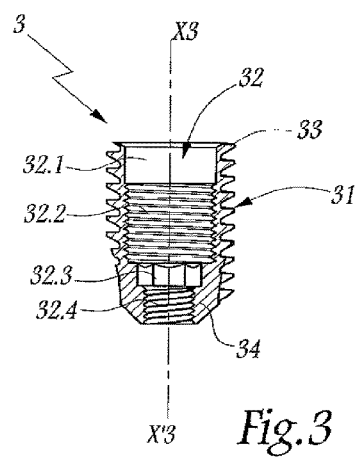
FIG. 3 illustrates a front axial cross-sectional view of a central fixation element of the glenoid implant of FIG. 1, according to embodiments of the present invention.

The central fixation element 3, shown in more detail in FIG. 3, is generally formed as a hollow cylinder of circular cross section, with a longitudinal geometric axis X3-X'3. The central element 3 is defined by an external lateral surface 31 which includes a self-tapping thread, and is traversed longitudinally by an opening 32, centered about the longitudinal axis X3-X'3, which extends between a superior end 33 and an inferior end 34 of the central element 3, according to embodiments of the present invention. The inferior end 34 is tronconical and its diameter becomes smaller as it approaches the inferior end 34, according to embodiments of the present invention.

The opening 32 includes a superior portion 32.1 that is cylindrical with a circular cross section, a tapping portion 32.2 of a diameter similar to the superior portion 32.1, a tool receptacle portion 32.3 with a hexagonal transversal cross section, and an inferior portion 32.4 that is cylindrical with a circular cross section and that is tapped and has a smaller diameter than the superior portion 32.1, according to embodiments of the present invention.

The central element 3 is made from a metal alloy or biocompatible ceramic, and its rigidity is higher than that of the articular body 2. For example, the central element 3 can be made from stainless steel, titanium, titanium alloy, cobalt-chrome alloy, and/or PEEK. The central element 3 is constructed so as to not deform in use.

The maximum transversal area of the central element 3, taken perpendicularly to the longitudinal axis X3-X'3, is smaller than the minimal transversal area of the plate 21 of the articular body 2, taken perpendicularly to the longitudinal axis X2-X'2. The portion of the largest section of the central element 3 is the superior threaded portion.

The contact between the central element 3 and the articular body 2 occurs only along a portion of the articular body 2, for example along the central protrusion 24, according to embodiments of the present invention. The central element 3 is not in contact with the entirety of the inferior surface 23 of the plate 21, according to embodiments of the present invention.

According to some embodiments of the present invention, the plate 21 is 1.8 to 5 times larger at its maximum transversal section than the central element 3. According to some embodiments of the present invention, the plate is 2.2 times larger at its maximum transversal section than the central element 3.

The central element 3 ensures anchoring of the articular body 2 in the glenoid via the central protrusion 24, but the central element 3 does not directly support the plate 21, according to embodiments of the present invention.

The screw 4, with a longitudinal geometric axis X4-X'4, includes a head 41 and a stem 44 that includes self-tapping threads, according to embodiments of the present invention. A blind hole 42 of hexagonal cross-section, centered on the axis X4-X'4, is formed in the head 41 of the screw 4. An external lateral surface 43 of the head 41 is threaded, and towards the top of the head 41 is a collar 45 with a larger diameter than the threaded portion 43. The screw 4 is made from a metallic material or biocompatible ceramic, such as a stainless steel, titanium, titanium alloy, and/or cobalt-chromium alloy, according to embodiments of the present invention.

As used herein, a threading or self-tapping thread is "to the right" when the driving action is performed with counterclockwise rotation, and is "to the left" when the driving action is performed with clockwise rotation. The threading of the lateral external surface 31 of the central element 3 is to the right, as shown by the arrow F3. The threading of the stem 44 of the screw 4 is to the left, as shown by the arrow F44, and the threading of the head 41 of the screw 4 and the self-tapping of the inferior portion 32.4 of the opening 32 are to the right, as shown by the arrow F41, according to embodiments of the present invention.

As the surgeon positions the glenoid implant 1 in the glenoid of the scapula, the surgeon first pierces a hole in the glenoid, of a diameter slightly smaller than the external diameter of the central element 3. Then, the surgeon screws the central element 3 into the glenoid, using a tool (not shown) equipped with a tip of hexagonal cross section which is inserted in the tool receptacle 32.3 of opening 32. The self-tapping threads of the central element 3 permit it to penetrate into the glenoid, more precisely into the preformed hole formed by the surgeon, while tapping it. The central element 3 permits by itself the fixation of the articular body 2 in the glenoid, according to embodiments of the present invention.

Next, the surgeon makes a hole in the glenoid, of a diameter slightly smaller than the diameter of the stem 44 of the screw 4, in passing the bit of a surgical drill through the opening 32 of the central element 3. The drill bit is guided by a tool (not shown) which permits passage of the drill bit through the bottom of the central element 3 while also protecting the threading 32.4 on the inside of the central element 3, according to embodiments of the present invention. The surgeon then slides or drives the head 41 of the screw 4 into the hole, with the help of a tool (not shown) equipped with a hexagonal tip which inserts into the blind hole 42 in the screw 4, according to embodiments of the present invention. The threading of the head 41 of the screw 4 cooperates with the threading of the inferior portion 32.4 of the opening 32. The axis X3-X'3 of the central element 3 is then substantially in alignment with the axis X4-X'4 of the screw 4. The threading of the head 41 is in the same direction as the threading of the stem 44 of the screw 4, which permits the surgeon, in the same movement, to screw the head 41 in the inferior portion 32.4 and to crew the stem 44 of the screw 4 into the hole which has been formed in the glenoid. The self-tapping threads of the stem 44 of the screw improve the anchoring of the screw 4 in the glenoid. Once in place, the collar 45 of the head 41 of the screw 4, which has a larger diameter than the inferior portion 32.4 of the opening 32, permits the retention of the head 41 in the opening 32 and prevents its passage through the opening 32.

According to one alternative embodiment, the threading of the head 41 of the screw 4 includes two threads, to facilitate the acceptance of the threading in the tapping of the inferior portion 32.4 of the opening 32. The pitch of the threading of the head 41 may be equal to the pitch of the threading of the stem 44 of the screw 4 to optimize the penetration of the screw 4 in the glenoid while the threading of the head 41 cooperates with the tapping of the inferior portion 32.4 of the opening 32, according to embodiments of the present invention.

The threading of the head 41 may also include a stop or a brake, such as for example a transverse pin of synthetic material, for preventing a loosening or disengagement of the screw, according to embodiments of the present invention.

Once the central element 3 and the screw 4 are placed in the glenoid, the sub-assembly formed by these two elements is locked in rotation, with respect to the glenoid, about the axes X3-X'3 and X4-X'4, due to the opposed directions of the threading of the stem 44 of the screw 4. In fact, when the subassembly tends to unscrew in the direction of the threading of the external lateral surface 31 of the central element 3, the rotation is locked by the threading of the stem 44 of the screw 4. On the other hand, when the subassembly tends to unscrew in the direction of the threading of the stem 44 of the screw 4, the rotation is locked by the threading of the external lateral surface 31 of the central element 3, according to embodiments of the present invention.

Before or after having placed the central element 3 and the screw 4, the surgeon pierces a lateral hole in the glenoid, adapted to receive the lateral post 26 of the articular body 2, according to embodiments of the present invention.

Once the central element 2 and the screw 4 are in place in the glenoid, the surgeon pushes in the central protrusion of the articular body 2 into the opening 32 of the central element 3, until the interior surface 23 of the plate 21 comes into contact against the superior end 33 of the central element. The axes X2-X'2, X3-X'3, and X4-X'4 are then coincident and overlapping with the axis X1-X'1 of the glenoid implant 1, according to embodiments of the present invention.

According to an alternative embodiment of the present invention, the surgeon pushes the central protrusion 24 into the opening 32 until the inferior side 23 of the plate 1 comes into contact against the glenoid, without the inferior side 23 being in contact with the superior end 33 of the central element. This can limit the wear of the articular body 2 against the central element 3, according to embodiments of the present invention.

The superior portion 24.1 of the central protrusion 24 is thus lodged in the superior portion 32.1 of the opening 32, and the intermediate portion 24.2 of the central portion 24 is thus lodged in the threads of the threaded portion 32.2 of the opening 32, and the fins 25 are thus retained between the threads through a complementarity of shapes and flexible deformation. The lateral post 26 becomes trapped in the corresponding hole formed in the glenoid, and prevents rotation of the articular body 2 about the axis X1-X'1 with respect to the glenoid, according to embodiments of the present invention.

The fins 25 prevent translation of the articular body 2, along the length of the axis X1-X'1, with respect to the central element 3, as long as the strength of the forces which are applied to the glenoid implant 1 do not surpass too significantly the strength of the forces undergone by the natural articulation of the shoulder.

Once the glenoid implant 1 is implanted in the glenoid, its rotation about the axis X1-X'1 with respect to the glenoid is locked. In fact, the lateral post 26 locks the rotation of the articular body 2 with respect to the glenoid, and the rotation, with respect to the glenoid, of the subassembly formed by the central element 3 and the screw 4, is locked due to the threading pitch being in a direction different from the central element 3 and the shaft 44 of the screw 4, according to embodiments of the present invention.

The locking of the rotation of the glenoid implant 1 with respect to the glenoid is effective, as it prevents the glenoid implant 1 from disengaging under the action of the mechanical forces resulting from the pressure and movements of the humeral head against the superior side 22 of the articular body 2.

The lateral post 26, which permits the locking of the articular body 2 in rotation about the axis X1-X'1 with respect to the glenoid, is optional and may be substituted for other rotational locking mechanisms, according to embodiments of the present invention. For example, the superior end of the external lateral surface of the central post 24 may extend superiorly of the central element 3, and its transversal cross section may be, for example, square or hexagonal, so as to lock the rotation of the articular body 2 with respect to the glenoid, once the central element 3 is placed into the glenoid, according to embodiments of the present invention. In such case, the surgeon prepares a sole cavity in the glenoid, composed of a portion for receiving the central element 3, aligned with a portion to receive the screw 4. Such a configuration may be particularly helpful as the bony tissue is thus in large part preserved.

FIGS. 5 to 8 illustrate another embodiment of a glenoid implant 101, which includes elements generally similar to elements described with respect to glenoid implant 1, augmented by 100.

Also, the glenoid implant 101, with longitudinal axis X101-X'101, includes an articular body 102 with a metal back, a central fixation element 103 for anchoring in the articular body 102 in the glenoid of a scapula, and a screw 104 for locking rotation of the central element 103 with respect to the scapula, according to embodiments of the present invention.

The articular body 102, shown from a bottom perspective view in FIG. 8, includes a plate 121 with a circular cross-sectional shape, perpendicular to a longitudinal axis X102-X'102 of the articular body 102. The plate 121 is defined by a superior side 122 and by an inferior side 123. An external lateral surface 126 of the plate 121 may be tronconical, according to embodiments of the present invention.

The superior side may be configured to receive a supplemental piece (not shown) adapted to articulate with the humerus. In the case of a reversed prosthesis, this supplemental piece is hemispherical, and an implant which includes a concave articular surface may be implanted in the humerus.

Four receptacles 121a, 121b, 121c and 121d in the form of truncated spheres are formed in the plate 121 and open toward both the superior side 122 and the inferior side 123, according to embodiments of the present invention.

Two inserts 105 include a spherical external surface and are received in the receptacles 121b and 121d. The inserts 105 are in rotational engagement with the articular body 102, according to embodiments of the present invention. The inserts 105 are each traversed by a threaded hole adapted to receive a screw 106. The screws 106 are represented by their axes 106 shown in FIG. 6.

The inferior side 123 of the plate 121 is provided with a central protrusion 124, with a longitudinal axis X102-X'102, which includes a superior portion 124.1 that is cylindrical with a circular cross-sectional shape, connected to the inferior side 123, and an inferior portion 124.2 that is tronconical, the diameter of which becomes smaller further from the plate 121.

The articular body 102 is traversed longitudinally by an opening 125, centered on the axis X102-X'102, which includes a superior threaded portion 125.1, and an inferior portion 125.2 with a circular cross-sectional shape. The threading of the superior portion 125.1 is configured to permit fixation to the articular body 102 of a supplemental piece adapted to articulate with the humeral head.

The articular body 102 is metallic and/or ceramic, according to embodiments of the present invention. For example, the articular body 102 may be made from stainless steel, titanium, an alloy of titanium, and/or an alloy of cobalt-chromium, according to embodiments of the present invention.

The central element 103, shown in more detail in FIG. 7, is generally formed as a cylinder with a circular cross-sectional shape, with a longitudinal axis X103-X'103. The central element 13 is defined by a lateral external surface 131 which includes a self-tapping thread, and is traversed longitudinally by an opening 132 which extends between a superior end 133 and an inferior end 134 of the central element 103. The inferior end 134 of the central element 3 is tronconical and its diameter gets smaller as it gets closer to the inferior end 134, according to embodiments of the present invention.

The opening 132 includes a superior portion 132.1 which is cylindrical, with a circular cross-sectional shape, a tronconical portion 132.2, of which the diameter gets smaller as it approaches the inferior end 134, a hexagonal portion 132.3, of which the transverse cross-sectional shape is a hexagon, a rounded part 132.4 in the form of a dome, of which the summit is oriented toward the bottom, and an inferior portion 132.5 which is cylindrical with a circular cross-sectional shape, according to embodiments of the present invention.

The central element 103 is metallic and ceramic, according to embodiments of the present invention. For example, the central element 103 may be formed of or made with stainless steel, titanium, titanium alloy, and/or cobalt-chrome alloy, according to embodiments of the present invention.

The maximum transverse cross-sectional dimension of the central element 103, taken perpendicularly to the longitudinal axis X103-X'103, is smaller than the transverse cross-sectional dimension of the plate 121 of the articular body 102, taken perpendicularly to the longitudinal axis X102-X'102. The maximum transverse cross-sectional dimension of the central element 103 is located at the level of the superior end 133, according to embodiments of the present invention. The contact between the central element 103 and the articular body 102 is made solely between a portion of the articular body 102, for example the central protrusion 124, and an annular zone of the inferior surface 123 surrounding the central protrusion 124, according to embodiments of the present invention. The central element 103 is not in contact with the entirety of the inferior surface 123 of the plate 121, according to embodiments of the present invention. The annular zone of pressure of the plate 121 on the central element 3 is relatively small with respect to the overall dimensions of the inferior surface 123, according to embodiments of the present invention.

The central element 103 ensures the anchoring of the articular body 102 in the glenoid, and the element central 103 does not support the plate 121, according to embodiments of the present invention.

The screw 104, having a longitudinal axis X104-X'104, includes a head 141 and a threaded stem 144 which may also be self-tapping, according to embodiments of the present invention. A blind hole 142 of square cross-sectional shape, centered on the longitudinal axis X104-X'104, is formed in the head 141 of the screw 104, according to embodiments of the present invention. A lateral external surface 13 of the head 141 is formed of a dome of which the summit is turned toward the bottom and of which the geometry is complementary to that of the rounded portion 132.4 of the opening 132 of the central element 103, according to embodiments of the present invention.

The screw 104 is metallic or ceramic, according to embodiments of the present invention. For example, the screw 104 may be formed from stainless steel, titanium, titanium alloy, and/or cobalt-chrome, according to embodiments of the present invention.

The threading of the external lateral surface 131 of the central element 103 is to the right, as shown by the arrow F131, while the threading of the stem 144 of the screw 104 is to the left, as shown by the arrow F144, according to embodiments of the present invention.

When the surgeon has achieved the placement of the glenoid implant 101 in the glenoid, the surgeon first forms a hole in the glenoid, of a diameter slightly smaller than the external diameter of the central element 103. Then, the surgeon inserts the central element 03 into the glenoid, for example with a tool (not shown), equipped with a hexagonal tip which is inserted into the hexagonal portion 132.3, according to embodiments of the present invention. The self-tapping threading of the central element 103 permits it to penetrate in the glenoid while also tapping. The surgeon makes a hole in the glenoid, of a diameter that is slightly smaller than the diameter of the stem 144 of the screw 104, in passing a drill bit (not shown) through the opening 132 of the central element 103. The drill bit is guided by a tool (not shown) which fits into one of the portions of the opening 132, according to embodiments of the present invention. The surgeon then inserts the screw 104 into the hole which has been formed, with the help of a tool (not shown) equipped with a square tip which is inserted into the blind hole 142 of the screw 104. Finally, the lateral external surface 141 of the screw 104 is in contact with the lateral surface of the portion 132.4 of the opening of the central element 103, according to embodiments of the present invention.

Once the central element 103 and the screw 104 are implanted in the glenoid, the sub-assembly formed by these two elements is locked in rotation, with respect to the glenoid, due to the opposed directions of the threading of the external surface 131 of the central element 103, with respect to the threading direction of the stem 144 of the screw 104, according to embodiments of the present invention.

Once the central element 103 and the screw 1034 are in place in the glenoid, the surgeon pushes in the central protrusion 124 of the articular body 102 into the opening 132 of the central element 103, until the tronconical portion of the interior surface 124.2 of the central protrusion 124 is coincident with the tronconical portion 132.2 of the opening 132. Such an assembly of a "Morse cone" permits the locking of the translation and the rotation of the articular body 102 with respect to the central element 103, as long as the strength of the forces which are applied thereto do not exceed the forces undergone by a natural articulation, according to embodiments of the present invention.

Also, if the surgeon removes the glenoid implant 101 from the scapula, the articular body 102 may be uncoupled from the central element 103 with appropriate tools, according to embodiments of the present invention.

The screws 106 are adapted to fix in a more stable manner the articular body 102 to the glenoid to lock as well the rotation of the articular body 102 with respect to the glenoid. The rotation of the inserts 105 in the receptacles 121b and 121d permits the screws 106 to be oriented in the desired manner and direction.

The articular body 106 may be fixed to the central element 103 prior to insertion of the screw 104 or before the insertion of the central element 103 into the glenoid, according to embodiments of the present invention.

Finally, the surgeon couples to the articular body 102 a supplemental piece adapted to articulate with the humeral head. This supplemental piece is inserted into the threading of the superior portion 125.1 of the receptacle 125. The supplemental piece includes a tronconical hollow adapted to mate with the lateral surface 126 of the plate 121, according to embodiments of the present invention.

FIGS. 9-10 illustrate a glenoid implant 201 according to another embodiment of the present invention, of which the elements similar to glenoid implant 1 carry the same reference numbers, augmented by 200.

The glenoid implant 201, with a longitudinal axis X201-X'201, also includes an articular body 202, for example of the "metal back" type, and a central element 203 for anchoring the articular body 202 into the glenoid of a scapula, according to embodiments of the present invention.

The articular body 202, with a longitudinal axis X202-X'202, includes a circular plate 221 which is perpendicular to the axis X202-X'202, which is defined by a superior side 222 and an inferior side 223. The plate 221 of the articular body 202 also includes a lateral surface 226. The inferior side 223 includes a central protrusion 224 which is cylindrical with a circular cross-sectional shape, centered on the axis X202-X'202. The central protrusion 224 is hollow and defines a tronconical receptacle 225, of which the diameter becomes smaller as it approaches the plate 221.

The superior side 222 of the plate 221 is adapted to receive a supplemental piece (not shown), configured to articulate with the humeral head.

The central element 203, with a longitudinal axis X203-X'203, includes a tronconical intermediate portion 203.2 with a diameter which gets smaller between a superior end 233 and an inferior end 234 of the central element 203. A lateral external surface 231 of the intermediate portion 203.2 includes a self-tapping threading and is traversed transversally by holes 238. The intermediate portion 203.2 includes near its bottom an inferior tronconical portion 203.3, which has a cone shape that is sloped at a greater angle with respect to the longitudinal axis X203-X'203 than the cone shape of the intermediate portion 203.2. The intermediate portion 203.2 includes near its top a tronconical superior portion 203.1, of which the diameter diminishes as it approaches the superior end 233, according to embodiments of the present invention. A peripheral groove 237 is defined between the intermediate portion 203.2 and the superior portion 203.1, according to embodiments of the present invention.

The central element 203 is traversed by a longitudinal opening 232, centered on the axis X203-X'203, which opens on both ends of the central element 203. The opening 232 includes a superior portion 232.1, with a hexagonal cross-sectional shape, and an inferior portion 232.2 which is cylindrical with a circular cross-sectional shape and which connects the superior portion 232.1 to the inferior end 234 of the central element 203, according to embodiments of the present invention.

The holes 238 are spaced or set off from one another along the intermediate portion 203.2 and open from the inferior portion 232.2 of the opening 232, according to embodiments of the present invention.

The maximum transverse cross-sectional dimension of the central element 203, taken perpendicularly to the longitudinal axis X203-X'203, is smaller than the transverse cross-sectional dimension of the plate 221 of the articular body 202, taken perpendicularly to the longitudinal axis X202-X'202. The contact between the central element 203 and the articular body 202 occurs solely along a portion of the articular body 202, for example on the central protrusion 224. The central element 203 is not in contact with the entirety of the inferior surface 223 of the plate 221. The central element 203 helps to ensure anchoring of the articular body 202 in the glenoid, and the central element 203 does not support the inferior surface 223 of the plate 221, according to embodiments of the present invention.

When placing the glenoid implant 201 in the scapula, the surgeon first forms a hole in the glenoid, with a diameter slightly smaller than the diameter of the central element. Next, the surgeon inserts the central element 203 into the glenoid, using a tool (not shown) equipped with a hexagonal tip which is inserted into the superior portion 232.1 of the opening 232, according to embodiments of the present invention.

The articular body 202 is assembled to the central element 203 in joining the central protrusion 224 to the superior portion 203.1 of the central element 203. When the articular body 202 is assembled to the central element 203, the articular body 202 is locked in translation and in rotation with respect to the central element 203, due to the fixation of the "Morse cone" type between the two elements.

Once the glenoid implant is implanted, the bony tissue of the glenoid colonizes the holes 238, which contributes to the locking of the rotation of the central element 203 with respect to the glenoid, and improves the longevity of the glenoid implant 201. The rotation of the articular body 202 with respect to the glenoid is locked via the screw and the inserts (not shown), similar to screws 106 and inserts 105, according to embodiments of the present invention.

FIGS. 11 to 12 illustrate a glenoid implant 301, according to another embodiment of the present invention, of which the elements similar to implant 1 have the same reference numbers augmented by 300.

The glenoid implant 301, with longitudinal axis X301-X'301, includes an articular body 302 and a central element 303 for anchoring the articular body 302 in the glenoid of a scapula, according to embodiments of the present invention.

The articular body 302, after its fixation to the glenoid, is adapted to articulate with a head, eventually a prosthetic head, of a humerus (not shown), of the patient with a view to reproducing an articular performance as close as possible to the performance of the patient's original shoulder, according to embodiments of the present invention.

The articular body 302, with a longitudinal axis X302-X'302, includes a plate 321, generally perpendicular to the axis X302-X'302, defined by a superior side 322 and an inferior side 323. The superior side 322 includes an articular surface for articulation of the scapula with a humeral head. The interior face 323 of the plate 321 includes a central protrusion 324, centered on the axis X302-X'302, of which the external lateral surface is hexagonal. The central protrusion 324 is hollow and defines a tronconical receptacle 325 of which the diameter increases in a direction away from the plate 321, according to embodiments of the present invention.

As shown in FIGS. 11 and 12, the plate 321 has an elongated form, and extends the length of the lengthwise axis Y321-Y'321, perpendicular to the axis X302-X'302. The central protrusion 324 is set back longitudinally, along the axis Y321-Y'321 with respect to the center C21 of the plate 321, according to embodiments of the present invention.

The articular body 302 is fabricated from one or two synthetic biocompatible materials and adapted for partial or total articulation, such as for example polyethylene, PEEK, and/or polyurethane, according to embodiments of the present invention.

The central element 303 is substantially the same as central element 303. Also, the central element 303 includes a tronconical intermediate portion 303.2 of which the diameter diminishes between the superior end 333 and the inferior end 334 of the central element 303. One lateral external surface of the intermediate portion 303.2 includes a self-tapping threading and is traversed transversally by holes 338 which are located at the base of the intermediate portion 303.3. The intermediate portion 303.2 includes near its bottom an inferior tronconical portion 303.3, of which the cone shape includes a more pronounced slope than that of the intermediate portion 303.2. The intermediate portion 303.2 includes near its top a superior tronconical portion 303.2. A peripheral groove 337 is formed between the intermediate portion 303.2 and the superior portion 303.1, according to embodiments of the present invention.

The central element 303 is traversed by a longitudinal opening 332, which opens from one end of the central element 303 to the other and communicates with the holes 338. The opening 332 includes a superior portion 332.1 of hexagonal cross-sectional shape, which opens onto the superior end 333, and an inferior portion 332.2 which is cylindrical and has a circular cross-sectional shape and which connects the superior portion 332.1 to the inferior end 334 of the central element 303, according to embodiments of the present invention.

The implantation of the glenoid implant 301 is similar to that described for implant 201, according to embodiments of the present invention. The hexagonal shape of the central protrusion 324 permits the locking of the rotation of the articular body 302 with respect to the glenoid.

Once the glenoid implant 301 is implanted, the bony tissue of the glenoid may recolonize the holes 338 and the opening 332, which helps to ensure locking of the rotation of the central element 303 with respect to the glenoid, and improves the durability and the longevity of the glenoid implant 301, according to embodiments of the present invention.

The locking of the rotation of the central element 303 with respect to the glenoid is achieved partially or exclusively by the middle of the articular body 302, according to embodiments of the present invention. In fact, due to the hexagonal cross-section of the central protrusion 324, the rotation of the articular body 302 with respect to the glenoid is locked. Taking into account the fact that the articular body 302 and the central element 303 are each locked in rotation with respect to the glenoid, no other locking means are needed, according to embodiments of the present invention. However, according to some embodiments of the present invention, the locking between the articular body 302 and the central element 303 is achieved with a mortise-and-tenon joint.

The maximum transverse cross-sectional dimension of the central element 303, taken perpendicularly to the longitudinal axis X303-X'303, is smaller than the transverse cross-sectional dimension of the plate 321 of the articular body 302, taken perpendicularly to the longitudinal axis X302-X'302. The contact between the central element 303 and the articular body 302 is achieved solely on a portion of the articular body, for example the central protrusion 324. The central element 33 is not in contact with the entirety of the inferior surface 323, according to embodiments of the present invention. The central element 303 ensures anchoring of the articular body 302 in the glenoid, and the inferior surface 323 of the plate 321 is not supported by the central element 303, according to embodiments of the present invention.

Figure 14:
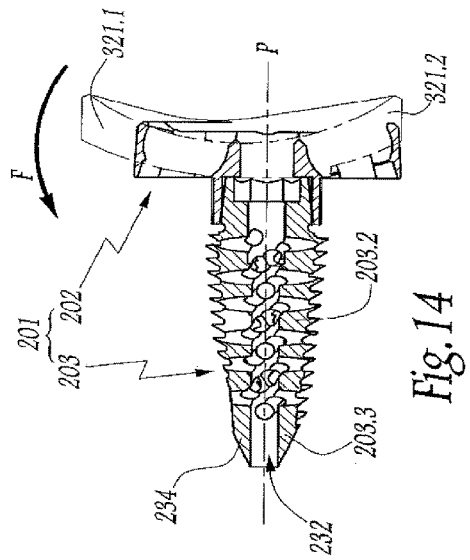
FIG. 14 illustrates an axial cross-sectional view of the glenoid implant of FIG. 9 with the articular body of the glenoid implant of FIG. 11 superimposed thereon, according to embodiments of the present invention.
Figure 13:
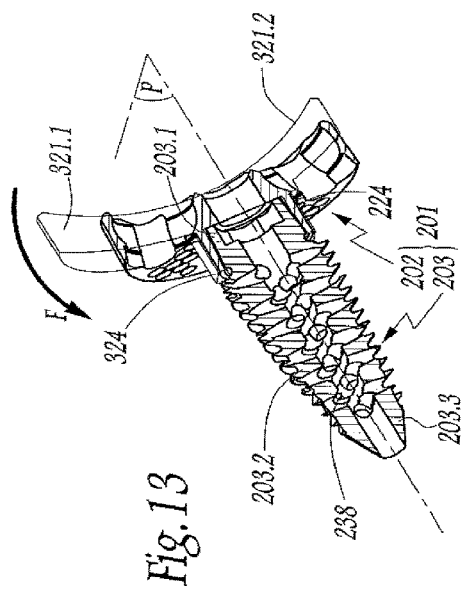
FIG. 13 illustrates a perspective axial cross-sectional view of the glenoid implant of FIG. 9 with the articular body of the glenoid implant of FIG. 11 superimposed thereon, according to embodiments of the present invention.

FIGS. 13 and 14 illustrates an articular body 202 and central element 203, according to embodiments of the present invention. The articular body 302 is superimposed upon the articular body 202, and is represented in a position in which it is assembled with the central element 203, according to embodiments of the present invention.

The lateral separation of the central protrusion 324 with respect to the lengthwise axis Y321-Y'321 of the plate 321 is shown in FIGS. 11 and 12, in which a portion of the length 321.1 of the plate 321, located across from a plane P which is perpendicular to the axis X302-X'302, laterally exceeds the articular body 202. A short portion 321.2 of the plate 321 is located on the other side of the plane P. When the surgeon implants the glenoid implant 301 in the scapula, he positions the articular body 301 in orienting the central protrusion 324 along the bottom, such that when the patient lifts his arm, the humeral head has a tendency to rotate the length portion 321.1 of the plate 321 towards the scapula, as shown by arrow F. The inferior face 323 of the long portion 321.1 is in direct contact with the glenoid, since the protrusion 324 is laterally separated, which permits the glenoid to receive directly the compression force which results from the tipping of the long portion 321.1, according to embodiments of the present invention.

Figure 16:
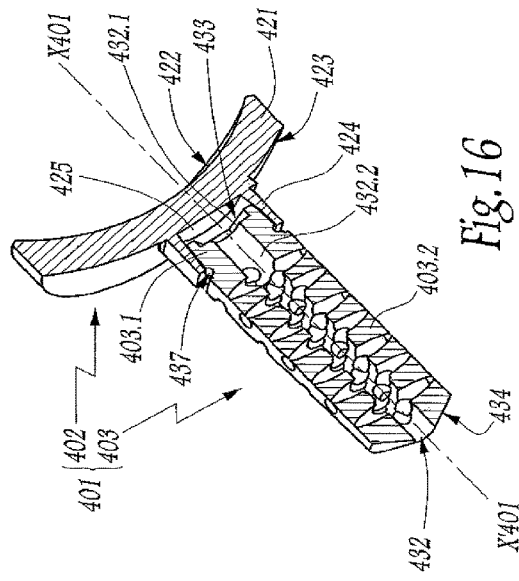
FIG. 16 illustrates a perspective axial cross-sectional view of the glenoid implant of FIG. 15, according to embodiments of the present invention.
Figure 15:
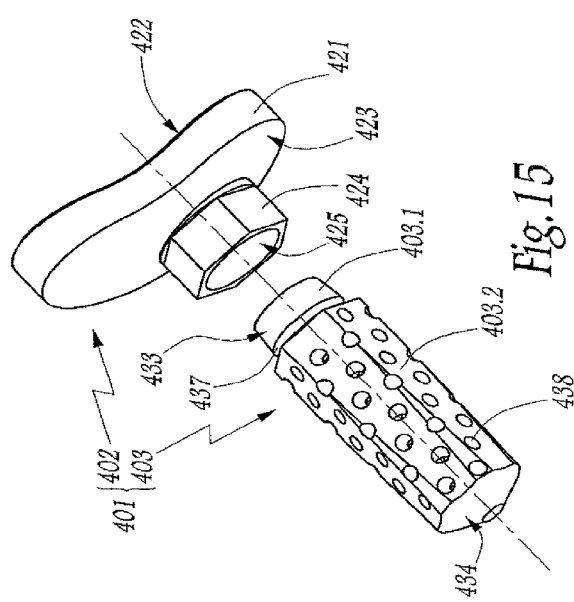
FIG. 15 illustrates an exploded perspective view of a glenoid implant according to another embodiment of the present invention.

FIGS. 15 and 16 illustrate a glenoid implant 401, according to embodiments of the present invention. The elements of glenoid implant 401 which are similar to the elements of glenoid implant 1 have the same reference numbers, augmented by 100.

The glenoid implant 401 includes an articular body 402, similar or the same as articular body 302, and a central element 403 of a "press fit" variety, for anchoring the articular body 402 in the glenoid of the scapula.

Also, the articular body 402, with a longitudinal axis X402-X'402, includes a plate 421, of which the superior face 422 includes an articular surface for articulation of the scapula with the humeral head, according to embodiments of the present invention. An inferior surface 423 of the plate 421 is provided with a central protrusion 424 having a hexagonal cross-sectional shape. The central protrusion 424 is hollow and defines a tronconical receptacle 425, of which the diameter diminishes as it approaches the plate 421, according to embodiments of the present invention.

The articular body 402 is made from one or two synthetic biocompatible materials, such as, for example, polyethylene, PEEK, and/or polyurethane, according to embodiments of the present invention.

The central element 403, with a longitudinal axis X403-X'403, includes an inferior portion 403.2 in the form of a prism with a hexagonal base. The central element 403 includes a superior end 433, and an inferior end 434. The lateral stops of the central element are beveled progressively in the direction of the inferior end 434. The inferior portion 403.2 is traversed transversally by holes 438. The inferior portion 403.2 extends towards the top along a superior portion 403.1. A peripheral groove 437 is formed between the superior portion 403.1 and the inferior portion 403.2, according to embodiments of the present invention.

The central element 403 is made from a metallic or biocompatible ceramic material, such as a stainless steel, titanium, titanium alloy, and/or carbon alloy, according to embodiments of the present invention.

The maximum transverse cross-sectional dimension of the central element 403, taken perpendicularly to the longitudinal axis X403-X'403, is smaller than the transverse cross-sectional dimension of the plate 421 of the articular body 302, taken perpendicularly to the longitudinal axis X402-X'402. The contact between the central element 403 and the articular body 402 occurs solely along a portion of the articular body 402, for example along the central protrusion 424. The central element 403 is not in contact with the totality of the inferior surface of the plate 421. The central element 403 ensures anchoring of the articular body 402 in the glenoid, and the inferior surface 423 of the plate 421 is not supported by the central element 403, according to embodiments of the present invention.

As the surgeon places the glenoid implant 401 in the glenoid, the surgeon first forms a hole in the glenoid with dimensions slightly smaller than those of the central element 403. Then, the surgeon impacts the central element 403 to introduce it into the hole. The penetration of the central element 403 in the glenoid is facilitated due to the lateral beveled stops. The rotation of the central element 403 with respect to the glenoid is locked due to the hexagonal shape of the transverse cross-section of the central element 403. The bony colonization in the holes 438 may also contribute to locking the rotation of the central element 403 with respect to the glenoid, according to embodiments of the present invention.

Next, the surgeon mounts the central protrusion 424 of the articular body 402 on the superior portion 403.1 of the central element 403. When the articular body 402 is assembled to the central element 403, the articular body 402 is locked in translation and in rotation with respect to the central element 403, due to the fixation of the Morse cone type between these two elements. The axes X402-X'402 and X403-X'403 are thus aligned and coincident with the longitudinal axis X401-X'401 of the glenoid implant.

The rotational locking of the articular body 402 with respect to the glenoid is ensured by the hexagonal cross-sectional shape of the central protrusion 424, and by the friction between the superior portion 403.1 of the central element 403 and the receptacle 425 of the central protrusion 424, according to embodiments of the present invention. Also, the glenoid implant 401 is locked in rotation, about the axis X401-X'401, with respect to the scapula, according to embodiments of the present invention.

Figure 17:
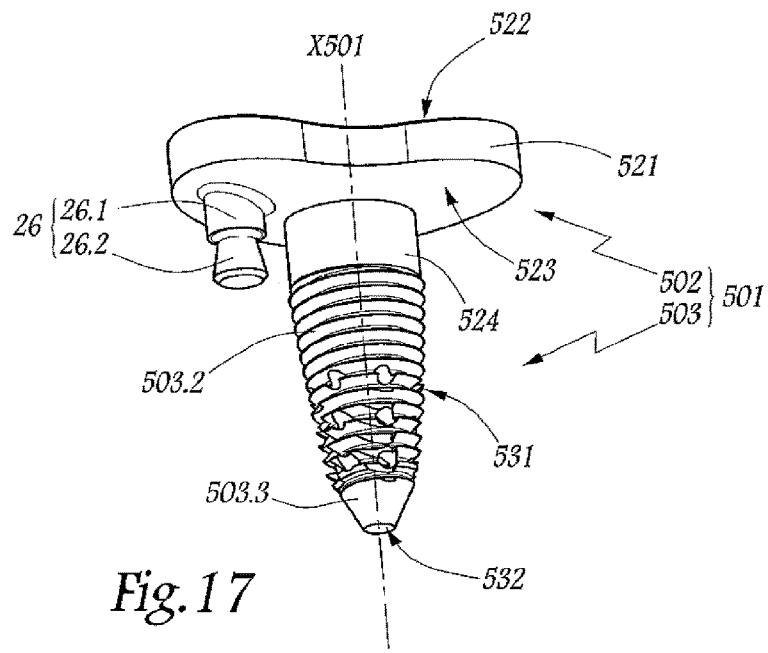
FIG. 17 illustrates a perspective view of a glenoid implant according to another embodiment of the present invention.
Figure 18:
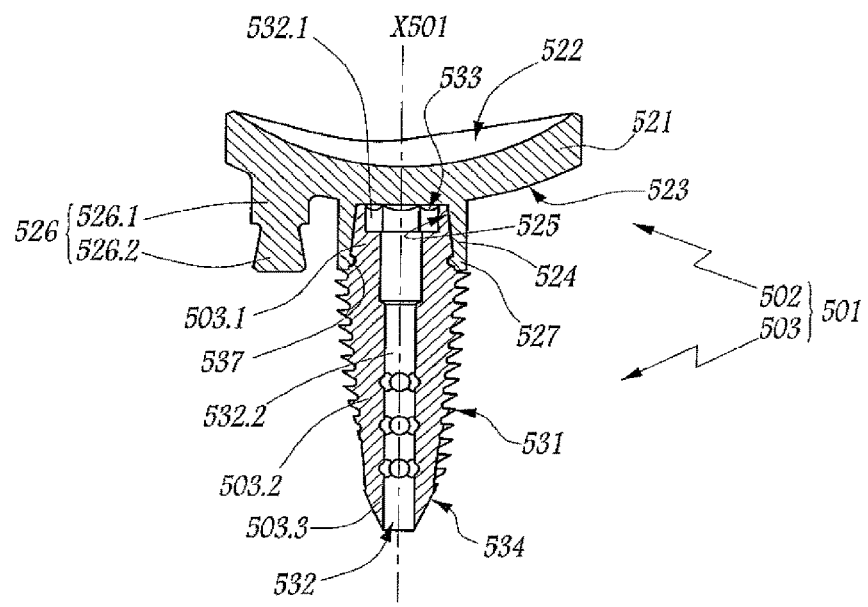
FIG. 18 illustrates a an axial cross-sectional view of the glenoid implant of FIG. 17, according to embodiments of the present invention.

FIGS. 17 and 18 illustrate a glenoid implant 501, according to embodiments of the present invention. The elements of glenoid implant 501 which are similar to glenoid implant 1 include the same reference numbers, augmented by 500.

The glenoid implant 501 includes an articular body 502, which may be similar to or the same as the articular body 302, and a central element 403 for anchoring the articular body 402 in the glenoid of the scapula, according to embodiments of the present invention.

The articular body 502 includes a plate 521 defined by a superior concave face 522, which includes an articular surface for articulation of the scapula with the humeral head, and by an inferior face 523, equipped with a central protrusion 524 that is cylindrical with a circular cross-sectional shape, according to embodiments of the present invention. The central protrusion 524 is hollow and defines a tronconical receptacle 525 of which the diameter increases along a direction away from the plate 521, according to embodiments of the present invention.

The inferior side 523 includes a lateral post 526, parallel to the central protrusion 524, which includes a superior portion 526.1 which is cylindrical with a circular cross-section, of a diameter that is smaller than the diameter of the central protrusion 524, which is connected to the inferior side 523 of the plate 521, according to embodiments of the present invention. The lateral post 526 includes a tronconical inferior portion 526.2, connected to the superior portion 526.1, of which the diameter increases in a direction away from the plate 521. The lateral internal surface of the central protrusion 524 may be provided with a peripheral fin 527, according to embodiments of the present invention.

The central element 503 includes a tronconical intermediate portion 503.2 of which the diameter decreases between a superior end 533 and an inferior end 534 of the central element 503, and which communicates with the holes 538. An external lateral surface 531 of the intermediate portion 503.2 includes a self-tapping threading and is traversed transversally by holes 538 which are located at the bottom of the intermediate portion 503.2, according to embodiments of the present invention. The intermediate portion 503.2 extends toward the base with an inferior tronconical portion 503.3, of which the conical shape has a slope that is higher than that of the intermediate portion 503.2. The intermediate portion 503.2 extends toward the top with a superior tronconical portion 503.1, of which the larger diameter is across from the intermediate portion 503.2. A peripheral groove 537 is formed at the interface between the superior portion 503.1 and the intermediate portion 503.2, according to embodiments of the present invention.

The central element 503 is traversed by a longitudinal opening 532, which opens toward both ends of the central element 503 and which communicates with the holes 538. The opening 532 includes a superior portion 532.1 of hexagonal transverse cross-sectional shape, which opens on the superior end 533, and an inferior portion 532.2 which is cylindrical with a circular cross-sectional shape and which connects the superior portion 532.1 to the inferior end 534 of the central element 503, according to embodiments of the present invention.

The maximum transverse cross-sectional dimension of the central element 503 is smaller than the transverse cross-sectional dimension of the plate of the articular body 502. The contact between the central element 503 and the articular body 502 occurs solely along a portion of the articular body 502, for example at the central protrusion 524, according to embodiments of the present invention. The central element 503 is not in contact with the entirety of the inferior surface 523 of the plate 521, according to embodiments of the present invention. The central element 503 ensures the anchoring of the articular body 502 in the glenoid, and the inferior surface 523 of the plate 521 is not supported by the central element 503, according to embodiments of the present invention.

As the glenoid implant 501 is positioned in the glenoid, the surgeon first forms a hole in the glenoid with dimensions slightly smaller than those of the central element 503, according to embodiments of the present invention. The surgeon may also form in the glenoid a reception hole for the lateral post 526. Then the surgeon inserts the central element 503 into the hole, using a tool equipped with a hexagonal tip, which may be inserted into the superior portion 532.1 of the opening 532 of the central element 503, according to embodiments of the present invention.

Then, the surgeon inserts the articular body 502 onto the superior portion 503.1 of the central element. The peripheral fin 527 positions itself in the groove 537 of the central element 503, which serves to lock the translation of the articular body 502 with respect to the central element. The lateral post 526 serves to lock the rotation of the articular body 502 with respect to the glenoid, according to embodiments of the present invention.

Once the glenoid is implanted, the bony tissue of the glenoid may recolonize the holes 538 and the opening 532, which contributes to locking the rotation of the central element 503 with respect to the glenoid and ameliorates the durability of the glenoid implant 501, according to embodiments of the present invention.

According to embodiments of the present invention, the central elements 203, 303, 403, 503 are configured to receive any one of a metallic or ceramic or synthetic articular body. In fact, the central element 203 of the glenoid implant 201 permits the fixation of a metallic or ceramic articular body, by means of the superior portion 203.1 which forms of cone of retention. In addition, the groove 237 of the central element 203 serves to couple a synthetic articular body provided with a peripheral fin similar to fin 527 of the articular body 502, according to embodiments of the present invention. Also, the central elements 303, 403 and 503 are provided, to the same end, with a tronconical portion 303.1, 403.1, 503.1 adapted to be capped with a tronconical receptacle 325, 425, 525 defined by an articular body that is metallic or ceramic, and by a groove 337, 437, 537 for coupling a synthetic articular body, according to embodiments of the present invention.

The threading of the tapped portion 32.2 may be replaced with grooves separated along the length of the axis X3-X'3. Also, the number of fins 25 may vary, according to embodiments of the present invention.

The articular body 2 may be formed of a metallic and/or ceramic material, such as pyrocarbon. Such a material may be configured to not deform, such that the fixation between the articular body 2 and the central element 3 is of a Morse cone type. Such fixation may replace the fins 25, according to embodiments of the present invention. PEEK may include a remarkable rigidity for a polymer; as such, a Morse cone type connection may be used to fix an element formed of PEEK, according to embodiments of the present invention.

Moreover, the articular bodies 302, 402 may be formed of a hard metallic material or a hard ceramic material, such as pyrocarbon, according to embodiments of the present invention.

According to an embodiment of the present invention, the superior portion 32.1 of the opening 32 as well as the superior portion 24.1 are tronconical instead of cylindrical.

According to another embodiment of the present invention, the threading of the lateral external surface 31 is to the left, while the threading of the shaft 44 of the screw 4 is to the right. In such case, the threading of the head 41 of the screw 4 is also to the right and the tapping of the inferior portion 32.4 of the opening is also to the right, according to embodiments of the present invention.

According to another embodiment of the present invention, the threading of the lateral external surface 131 is to the left, while the threading of shaft 144 of the screw 104 is to the right.

According to another embodiment of the present invention, the portion 132.1 of the opening 132 is tronconical and the portion 132.2 is cylindrical, according to embodiments of the present invention.

According to another embodiment of the present invention, the screws 4 and 104 are made of polymer, for example PEEK.

According to yet another embodiment of the present invention, the inferior portion 124.2 of the central protrusion 124 is cylindrical with a circular cross-sectional shape. In this case, the portion 132.2 is also cylindrical with a circular cross-sectional shape and is adapted to receive the inferior portion 124.2 of the central post 124, such that the fixation of the articular body 102 is achieved by inserting the central pin 124 into the central element 103 with force.

According to another embodiment of the present invention, the central element defines a receptacle for a central protrusion of an articular body. For example, to be adapted to receive a synthetic articular body, the receptacle for a central element may include an internal threading, similar to the threading of the threaded portion 32.2 of the central element 32, into which the aforementioned fins clip along the length of the central protrusion, according to embodiments of the present invention. In order to be adapted to receive a metallic or ceramic articular body, the central element may include a tronconical receptacle for a central tronconical protrusion of the articular body, according to embodiments of the present invention.

The hexagonal portion 32.3 of the central element 3 and the blind hole 42 of the head of the screw 4 may include a square cross-sectional shape, for example in the form of a cross, a receptacle in the shape of Torx®, or some other geometry permitting the use of a tool, according to embodiments of the present invention. Other embodiments may also include such features, for example the blind hole 142 of the screw 104 and the hexagonal portion 132.2 of the central element 103. Various tools with different tips may be used depending on the types of screws or screw heads used.

The articular body 102 and 202 may be equipped with two supplemental inserts 105 received in the receptacles 121a and 121c or 221a and 221c, according to embodiments of the present invention.

According to some embodiments of the present invention, a means comprised by the central fixation element for mechanically engaging with the central protrusion may include, without limitation, elements 32.1 and 32.2; elements 132.1 and 132.2; elements 203.1 and 237; elements 303.1 and 337; elements 403.1 and 437; and elements 503.1 and 537. According to some embodiments of the present invention, a first means for locking rotation of the central fixation element with respect to the glenoid may include, without limitation, elements 31 and 4; 131 and 104; 238; 338; 403.2 and 438; and 538. According to some embodiments of the present invention, a second means for locking rotation of the articular body with respect to the glenoid may include, without limitation, elements 26; 106; 324; 424; and 526.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A glenoid implant for a shoulder prosthesis for implantation in the glenoid of a scapula, the glenoid implant comprising:
   an articular portion configured for articulation with a humerus, the articular portion comprising a plate, the plate comprising a side configured to be oriented toward the glenoid, the side comprising a central element defining a recess extending between a first end located adjacent to the plate and a second end opposite the plate, the recess comprising:
   a proximal portion comprising a first threaded wall pattern,
   an intermediate portion comprising a non-threaded wall pattern; and
   a distal portion comprising a second threaded wall pattern; and
   a distal anchor screw comprising a proximal head and a stem extending distally from the proximal head, the proximal head being configured to engage the central element.

2. The glenoid implant of claim 1, wherein when central element of the articular portion engages the proximal head of the distal anchor screw, at least a portion of the proximal head is disposed in the intermediate portion of the central element.

3. The glenoid implant of claim 1, wherein the proximal head comprises an external surface comprising a third threaded pattern, and wherein the stem comprises an external surface comprising a fourth threaded pattern.

4. The glenoid implant of claim 3, wherein the third threaded pattern is different from the fourth threaded pattern.

5. The glenoid implant of claim 1, further comprising a peripheral locking mechanism configured to lock rotation of the articular body with respect to the glenoid.

6. The glenoid implant of claim 5, wherein the peripheral locking mechanism is a lateral post extending from the side of the plate configured to be oriented toward the glenoid.

7. The glenoid implant of claim 5, wherein the peripheral locking mechanism comprises a receptacle configured to receive a bone screw.

8. A glenoid implant for a shoulder prosthesis for implantation in the glenoid of a scapula, the glenoid implant comprising:
   an articular portion configured for articulation with a humerus, the articular portion comprising a plate, the plate comprising a side configured to be oriented toward the glenoid, the side comprising a central element defining a recess extending between a first end located adjacent to the plate and a second end opposite the plate, the recess comprising:
   a proximal portion comprising a first transverse dimension,
   an intermediate portion comprising a second transverse dimension that is different from the first transverse dimension; and
   a distal portion comprising a third transverse dimension that is different from the first transverse dimension; and
   a distal anchor screw comprising a proximal head and a stem extending distally from the proximal head, the proximal head being configured to engage the central element, the proximal head comprising an external surface comprising a threaded pattern, the stem comprising an external surface comprising a different threaded pattern,
   wherein the proximal portion of the recess further comprises a first threaded wall pattern, and wherein the distal portion of the recess further comprises a second threaded wall pattern, the second threaded wall pattern being spaced apart from the first threaded wall pattern by a non-threaded wall pattern.

9. The glenoid implant of claim 8, wherein when central element of the articular portion engages the proximal head of the distal anchor screw, at least a portion of the proximal head is disposed in the intermediate portion of the central element.

10. The glenoid implant of claim 8, further comprising a peripheral locking mechanism configured to lock rotation of the articular body with respect to the glenoid.

11. The glenoid implant of claim 10, wherein the peripheral locking mechanism is a lateral post extending from the side of the plate configured to be oriented toward the glenoid.

12. The glenoid implant of claim 10, wherein the peripheral locking mechanism comprises a receptacle configured to receive a bone screw.

* * * * *